United States Patent
Pan et al.

(10) Patent No.: US 10,729,821 B1
(45) Date of Patent: Aug. 4, 2020

(54) METHOD FOR PREPARING CHITOSAN/HEPARINIZED GRAPHENE OXIDE COMPOSITE MULTILAYER FILM ON SURFACE OF MEDICAL MAGNESIUM ALLOY

(71) Applicant: HUAIYIN INSTITUTE OF TECHNOLOGY, Huai'an (CN)

(72) Inventors: Changjiang Pan, Huai'an (CN); Tao Liu, Huai'an (CN); Tao Gong, Huai'an (CN); Lincai Zhang, Huai'an (CN); Wei Ye, Huai'an (CN)

(73) Assignee: HUAIYIN INSTITUTE OF TECHNOLOGY, Huai'an (CN)

( * ) Notice: Subject to any disclaimer, the term of this patent is extended or adjusted under 35 U.S.C. 154(b) by 360 days.

(21) Appl. No.: 15/768,904

(22) PCT Filed: May 27, 2017

(86) PCT No.: PCT/CN2017/086281
§ 371 (c)(1),
(2) Date: Apr. 17, 2018

(87) PCT Pub. No.: WO2018/196088
PCT Pub. Date: Nov. 1, 2018

(30) Foreign Application Priority Data

Apr. 28, 2017 (CN) .......................... 2017 1 0297089

(51) Int. Cl.
*A61L 31/10* (2006.01)
*A61L 31/02* (2006.01)
*A61L 31/12* (2006.01)

(52) U.S. Cl.
CPC ............. *A61L 31/10* (2013.01); *A61L 31/022* (2013.01); *A61L 31/128* (2013.01);
(Continued)

(58) Field of Classification Search
CPC .......... A61L 31/02; A61L 31/08; A61L 31/10; A61L 31/12; A61L 31/14; A61L 31/16
(Continued)

(56) References Cited

U.S. PATENT DOCUMENTS

2002/0087123 A1* 7/2002 Hossainy ............ A61L 33/0011
604/198
2007/0244569 A1* 10/2007 Weber ................... A61L 31/148
623/23.75
2016/0129162 A1* 5/2016 Pulugurtha ............. A61L 31/10
623/1.46

FOREIGN PATENT DOCUMENTS

CN 105327406 A * 2/2016
CN 105343890 A * 2/2016
(Continued)

OTHER PUBLICATIONS

Meng et al. The effect of a layer-by-layer chitosan—heparin coating on the endothelialization and coagulation properties of a coronary stent system. Biomaterials. 30. 2009. pp. 2276-2283 (Year: 2009).*
(Continued)

*Primary Examiner* — Cachet I Proctor
(74) *Attorney, Agent, or Firm* — CBM Patent Consulting, LLC

(57) ABSTRACT

A method for preparing a chitosan/heparinized graphene oxide composite multilayer film on the surface of a medical magnesium alloy comprises the following steps: firstly preparing negatively charged heparinized graphene oxide; then performing surface chemical treatment and self-assembly of 16-phosphonohexadecanoic acid molecules on the medical magnesium alloy; further covalently immobilizing chitosan on the surface of the magnesium alloy, thereby constructing a positively charged material surface; finally, alternately immersing the surface-modified magnesium alloy material in heparinized graphene oxide and a chitosan solution, and
(Continued)

then fully adsorbing, and obtaining the chitosan/heparinized graphene oxide composite multilayer film after drying. The surface modification of the medical magnesium alloy by adopting the method of the present invention can significantly improve the corrosion resistance and biocompatibility of the magnesium alloy to lay a foundation for the application of the magnesium alloy in the field of implantable medical devices such as vascular stents.

9 Claims, 1 Drawing Sheet

(52) U.S. Cl.
CPC ... *A61L 2300/232* (2013.01); *A61L 2300/236* (2013.01); *A61L 2300/418* (2013.01); *A61L 2420/06* (2013.01); *A61L 2420/08* (2013.01)

(58) Field of Classification Search
USPC ....................................................... 427/2.24
See application file for complete search history.

(56) References Cited

FOREIGN PATENT DOCUMENTS

EP            1535952 A1 *  6/2005  .............. C08J 3/246
KR      20160117662 A  * 10/2016

OTHER PUBLICATIONS

Zhao et al. Effect of the graphene oxide additive on the corrosion resistance of the plasma electrolytic oxidation coating of the AZ31 magnesium alloy. Corrosion Science. Volume 114. Jan. 2017 pp. 146-155 (Year: 2017).*

Cui et al. Corrosion resistance of biodegradable polymeric layer-by-layer coatings on magnesium alloy AZ31. Front. Material Science. vol. 10 (2). 2016. pp. 134-146 (Year: 2016).*

* cited by examiner

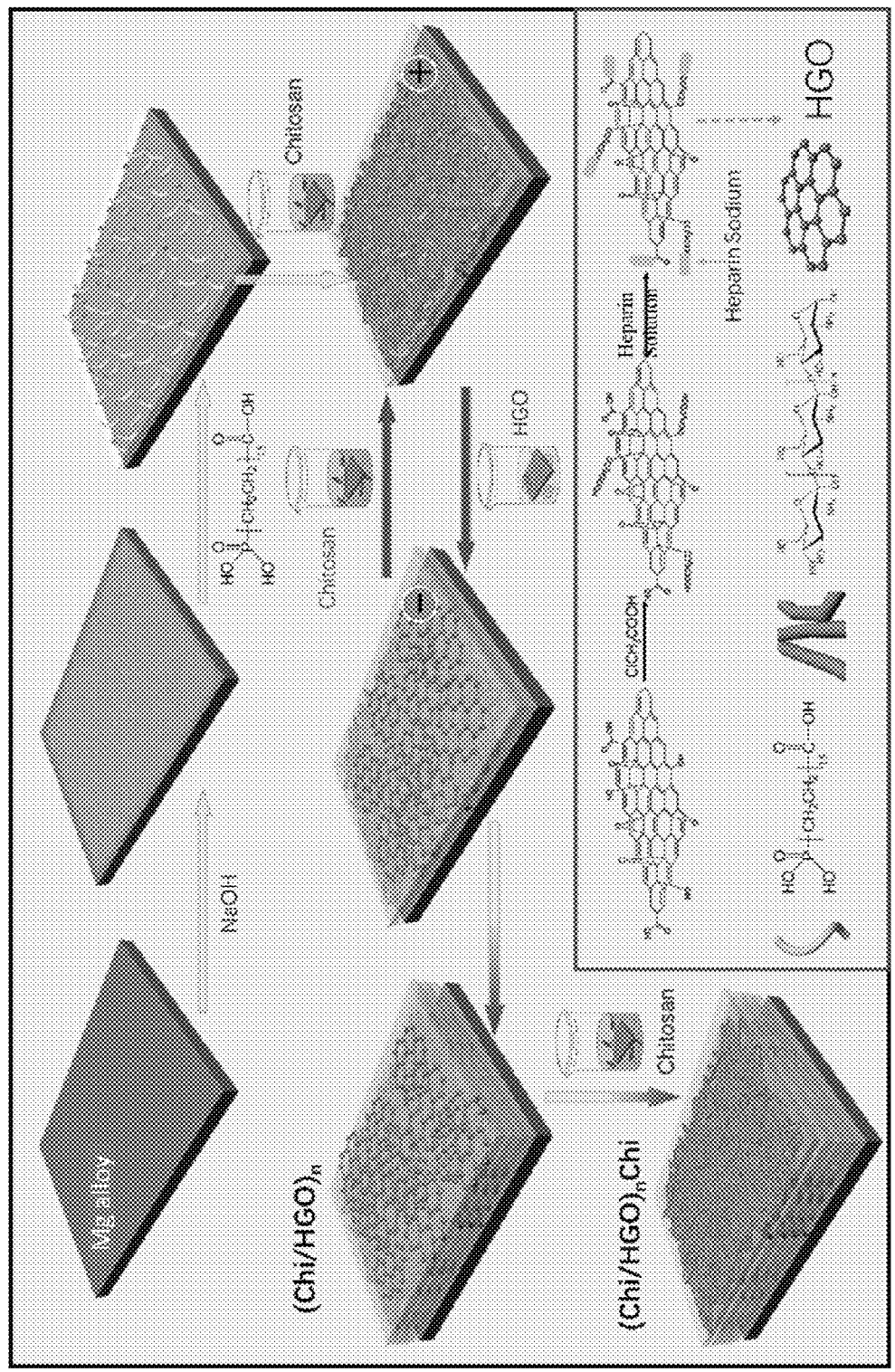

METHOD FOR PREPARING CHITOSAN/HEPARINIZED GRAPHENE OXIDE COMPOSITE MULTILAYER FILM ON SURFACE OF MEDICAL MAGNESIUM ALLOY

TECHNICAL FIELD

The present invention relates to the technical field of biomedical materials and medical devices, and more particularly relates to a method for preparing a chitosan/heparinized graphene oxide composite multilayer film on the surface of a medical magnesium alloy.

BACKGROUND

The stenosis induced by cardiovascular and cerebrovascular lesion is one of the most important reasons of complications of many fatal cardiovascular and cerebrovascular diseases. Metal vascular stent implantation is one of the main methods for treating stenotic cardiovascular and cerebrovascular diseases. In recent years, the magnesium alloy has become a research hotspot of cardiovascular stent biomaterials due to its excellent mechanical properties and biodegradable properties, and non-toxicity of its degradation products to the human body.

However, the magnesium alloy is rapidly degraded under physiological conditions due to its active chemical property, so that excess hydrogen is easily generated around the implanted tissues and a local alkaline increase in surrounding tissues and the accumulation of the secondary corrosion products are caused, resulting in premature loss of mechanical properties, poor blood compatibility and cell compatibility of the material, and toxic reactions to surrounding tissues, eventually leading to delayed healing of tissues and even implantation failure. The corrosion behavior and biocompatibility of the material are closely related to the surface properties of the material, therefore, the electrochemical degradation behavior of the magnesium alloy can be regulated, the blood compatibility can be improved and the endothelial tissue healing can be promoted through surface modification of the material as a vascular stent material, which is of great significance to its clinical application.

In view of the problem of too rapid degradation of the magnesium alloy in a physiological environment, the corrosion resistance of the magnesium alloy is mainly improved from both aspects of alloying and surface modification. The alloying can significantly improve the mechanical properties of the magnesium alloy, but the corrosion resistance of the prepared magnesium alloy in the complex physiological environment remains to be improved, and most of the alloying elements cannot effectively improve the biocompatibility of the material. Therefore, the surface of the magnesium alloy prepared by alloying is usually lack of biological activity.

At present, the research on improving the corrosion resistance of the magnesium alloy through surface modification mainly focuses on three aspects. One is to form a chemical conversion layer on the surface by surface chemical treatment or electrochemical treatment; the other is to form a surface modified layer by changing the microstructure of the surface; the third is to form a surface covering layer on the surface of magnesium alloy by introducing organic molecules and macromolecules, or preparing inorganic non-metallic coatings on the surface. The conversion layer or covering layer with better corrosion resistance formed on the surface through these methods can isolate a matrix from the surrounding medium, thereby effectively improving the corrosion resistance of the magnesium alloy and significantly reducing the physiological side reactions caused by rapid degradation, and thus improving the biocompatibility of the material to a certain degree.

The introduction of bioactive molecules on the surface is one of the most effective methods for improving the biocompatibility of the magnesium alloy and other biological materials. However, the surface modification strategy for non-degradable biomaterials often needs to be performed in electrolyte solutions, so that the corrosion degradation of magnesium alloy may be caused due to the active chemical property of the magnesium alloy, and thus the corrosion resistance of the magnesium alloy should be firstly improved before using these strategies. Although a great deal of effective work has been performed on the surface modification of the magnesium alloy, the current surface modification method of the magnesium alloy as an intravascular implant material does not achieve clinically satisfactory results in both aspects of improving the corrosion resistance and enhancing the biocompatibility. The surface layer constructed by surface chemical polymerization, self-assembly surface modification, and surface in-situ biological molecule immobilization technology and so on is thinner, has fewer biomolecules, and is limited in the improvement on the corrosion resistance and biocompatibility of the magnesium alloy. In the degradation process of the material, the surface biomolecules are firstly degraded and lost, and the magnesium alloy will soon lose its biological activity; various macromolecules or ceramic coatings have significant effects in improving the corrosion resistance of magnesium alloy, but may still cause blood coagulation and delayed healing of endothelium when used as an intravascular implant material.

SUMMARY OF THE INVENTION

The object of the present invention is to provide a method for preparing a chitosan/heparinized graphene oxide composite multilayer film on the surface of a medical magnesium alloy in order to overcome the defects of the prior art. A magnesium alloy surface with multifunctional characteristics can be constructed by the method, the corrosion resistance and biocompatibility of the magnesium alloy under physiological conditions are significantly enhanced, and the implantation success rate of the material and devices thereof is improved.

The technical scheme adopted by the present invention is as follows:

The method for preparing the chitosan/heparinized graphene oxide composite multilayer film on the surface of the medical magnesium alloy comprises the following steps:

1) firstly preparing negatively charged heparinized graphene oxide (HGO);

2) then performing surface chemical treatment and self-assembly surface modification on the medical magnesium alloy;

3) further covalently immobilizing chitosan (Chi) on the surface of the magnesium alloy, thereby constructing a positively charged material surface;

4) alternately immersing the surface-modified magnesium alloy material in HGO and Chi solution, and then fully adsorbing; and 5) finally, obtaining the Chi/HGO composite multilayer film after drying.

According to a further improved scheme of the present invention, in step 1), a method for preparing the heparinized graphene oxide comprises the following steps:

1.1) firstly, ultrasonically dispersing the graphene oxide in an NaOH solution having a concentration in the range of 0.1 to 0.5 mol/L for 2 hours;
1.2) then adding excess chloroacetic acid to ultrasonically react for 2 to 4 hours;
1.3) repeatedly centrifuge the solution to be neutral to remove impurities to obtain carboxylated graphene oxide;
1.4) ultrasonically dispersing the resulting carboxylated graphene oxide;
1.5) adding to a mixed solution of N,N'-dicyclohexylcarbodiimide and 4-(dimethylamino)pyridine to perform an oscillation reaction for 2 to 4 hours;
1.6) repeatedly and centrifugally washing the solution to remove impurities;
1.7) adding the activated graphene oxide to a heparin solution to fully react for 4 to 12 hours; and
1.8) finally obtaining HGO after repeatedly centrifugal washing.

According to a still further improved scheme of the present invention, in step 1.5), the molar ratio of N, N'-dicyclohexylcarbodiimide and 4-(dimethylamino) pyridine is 3 to 1 in the mixed solution of N, N'-dicyclohexylcarbodiimide and 4-(dimethylamino) pyridine.

According to a still further improved scheme of the present invention, in step 2), the chemical treatment on the magnesium alloy surface comprises the following steps:

firstly washing the magnesium alloy and then immersing in the NaOH solution having a concentration in the range of 1 to 5 mol/L, and treating at a temperature of 60 to 85° C. for 8 to 24 hours.

According to a still further improved scheme of the present invention, in step 2), the self-assembly method comprises the following steps:

immersing the magnesium alloy treated by NaOH in a 16-phosphonohexadecanoic acid solution having a concentration in the range of 1 to 10 mmol/L to react for 12 to 24 hours, and taking a sample out and then treating in vacuum at a temperature of 110° C. for 12 to 24 hours.

According to a still further improved scheme of the present invention, in step 3), the covalent immobilizing method of chitosan comprises the following steps:

3.1) immersing the surface-modified sample obtained in step 2) in a mixed solution of N-(3-dimethylaminopropyl)-N'-ethylcarbodiimide/N-hydroxysuccinimide to react;
3.2) drying after reacting for 2 to 8 hours;
3.3) after drying, continuously reacting by immersing in a chitosan solution having a concentration in the range of 1 to 5 g/L; and
3.4) after continuously reacting for 2 to 8 hours, washing and drying the sample to obtain a chitosan-modified positively charged magnesium alloy.

According to a still further improved scheme of the present invention, in step 3.1), the molar ratio of N-(3-dimethylaminopropyl)-N'-ethylcarbodiimide to N-hydroxysuccinimide is 4 to 1 in the mixed solution of N-(3-dimethylaminopropyl)-N'-ethylcarbodiimide/N-hydroxysuccinimide.

According to a still further improved scheme of the present invention, in a step 4), the method for preparing the chitosan/heparinized graphene oxide composite multilayer film comprises the following steps:

alternately immersing the material obtained in step 3) in the heparinized graphene oxide having a concentration in the range of 0.1 to 1 mg/ml and the chitosan solution having a concentration in the range of 1 to 5 g/L, adsorbing for 20 to 60 minutes every time, and then fully drying after adsorbing every time, thereby obtaining the Chi/HGO composite multilayer film.

According to a still further improved scheme of the present invention, the more the times of alternate immersion are, the thicker the thickness of the Chi/HGO composite multilayer film is.

The present invention has the following beneficial effects:

Firstly, according to the method for preparing the chitosan/heparinized graphene oxide composite multilayer film on the surface of the medical magnesium alloy provided by the present invention, an innovative design strategy is provided to solve the key technical problems of too rapid degradation rate and poor biocompatibility of the magnesium alloy biomaterials by constructing the chitosan/heparinized graphene oxide multilayer film coating by comprehensively adopting various surface treatment technologies.

Secondly, according to the method for preparing the chitosan/heparinized graphene oxide composite multilayer film on the surface of the medical magnesium alloy provided by the present invention, the magnesium alloy surface modification technology used in the present invention can not only improve the corrosion resistance of the magnesium alloy, but also significantly increase the biocompatibility of the magnesium alloy, and different coating thicknesses can be used to regulate and optimize the electrochemical behavior and biocompatibility of the magnesium alloy, thereby achieving the perfect match of electrochemical behavior and biocompatibility.

Thirdly, according to the method for preparing the chitosan/heparinized graphene oxide composite multilayer film on the surface of the medical magnesium alloy provided by the present invention, the Chi/HGO multilayer film coating constructed by the present invention is gradually degraded in the physiological environment, and gradually releases chitosan and HGO during the degradation process, so that the biological activities of different substances can be realized, and higher bioactivity and biocompatibility of the coating can be kept for a long time due to the gradual degradation of the coating, and thus the implantation success rate of the magnesium alloy material can be significantly improved.

Finally, according to the method for preparing the chitosan/heparinized graphene oxide composite multilayer film on the surface of the medical magnesium alloy provided by the present invention, due to good corrosion resistance of the chemical conversion layer after alkali heat treatment, the covering effect of heparinized graphene oxide and chitosan on the surface of magnesium alloy, the effect of chitosan on promoting endothelial cell growth, and the excellent anticoagulant properties and the function of selectively promoting endothelial cell growth of heparin, the multilayer film coating constructed by the present invention will fundamentally solve the problems of too rapid corrosion degradation and poor biocompatibility of the magnesium alloy, and can be used for surface modification of medical devices such as vascular stents.

BRIEF DESCRIPTION OF THE DRAWINGS

FIG. 1 is the schematic diagram of a method for preparing a chitosan/heparinized graphene oxide composite multilayer film on the surface of a medical magnesium alloy.

The following steps are included herein:
(1) carboxylated modification of graphene oxide;
(2) preparation of heparinized graphene oxide;

(3) alkali heat treatment of the surface of a magnesium alloy;

(4) surface self-assembly;

(5) covalent immobilization of chitosan on the surface of a magnesium alloy;

(6) preparation of a chitosan/heparinized graphene oxide composite multilayer film.

DETAILED DESCRIPTION OF THE INVENTION

As can be seen from FIG. 1, the present invention comprises the following steps:

1) firstly preparing negatively charged heparinized graphene oxide (HGO);

2) then performing surface chemical treatment and self-assembly surface modification on the medical magnesium alloy;

3) further covalently immobilizing chitosan (Chi) on the surface of the magnesium alloy, thereby constructing a positively charged material surface;

4) alternately immersing the surface-modified magnesium alloy material in HGO and a Chi solution, and then fully adsorbing; and 5) finally, obtaining the Chi/HGO composite multilayer film after drying.

According to a further improved scheme of the present invention, in step 1), a method for preparing the heparinized graphene oxide comprises the following steps:

1.1) firstly, ultrasonically dispersing the graphene oxide in a NaOH solution having a concentration of 0.3 mol/L for 2 hours;

1.2) then adding excess chloroacetic acid to ultrasonically react for 3 hours;

1.3) repeatedly and centrifugally washing the solution to be neutral to remove impurities to obtain carboxylated graphene oxide;

1.4) ultrasonically dispersing the resulting carboxylated graphene oxide;

1.5) adding to a mixed solution of N,N'-dicyclohexylcarbodiimide and 4-(dimethylamino)pyridine to perform an oscillation reaction for 3 hours;

1.6) repeatedly and centrifugally washing the solution to remove impurities;

1.7) adding the activated graphene oxide to a heparin solution to fully react for 10 hours; and 1.8) finally obtaining HGO after repeatedly centrifugal washing.

In step 1.5), the molar ratio of N,N'-dicyclohexylcarbodiimide and 4-(dimethylamino) pyridine is 3 to 1 in the mixed solution of N,N'-dicyclohexylcarbodiimide and 4-(dimethylamino) pyridine.

In step 2), the chemical treatment of the magnesium alloy surface comprises the following steps: firstly washing the magnesium alloy and then immersing in the NaOH solution having a concentration of 3 mol/L, and treating at a temperature of 60 to 85° C. for 15 hours.

In step 2), the self-assembly method comprises the following steps:

immersing the magnesium alloy treated by NaOH in a 16-phosphonohexadecanoic acid solution having a concentration in the range of 7 mmol/L to react for 18 hours, and taking a sample out and then treating in vacuum at a temperature of 110° C. for 20 hours.

In step 3), the covalent immobilizing method of chitosan comprises the following steps:

3.1) immersing the surface-modified sample obtained in step 2) in a mixed solution of N-(3-dimethylaminopropyl)-N'-ethylcarbodiimide/N-hydroxysuccinimide to react;

3.2) drying after reacting for 5 hours;

3.3) after drying, continuously reacting by immersing in a chitosan solution having a concentration of 3 g/L; and 3.4) after continuously reacting for 6 hours, washing and drying the sample to obtain a chitosan-modified positively charged magnesium alloy.

In step 3.1), the molar ratio of N-(3-dimethylaminopropyl)-N'-ethylcarbodiimide to N-hydroxysuccinimide is 4 to 1 in the mixed solution of N-(3-dimethylaminopropyl)-N'-ethylcarbodiimide/N-hydroxysuccinimide.

In step 4), the method for preparing the chitosan/heparinized graphene oxide composite multilayer film comprises the following steps:

alternately immersing the material obtained in step 3) in the heparinized graphene oxide having a concentration of 0.4 mg/ml and the chitosan solution having a concentration of 3 g/L, adsorbing for 30 minutes every time, and then fully drying after adsorbing every time, thereby obtaining the Chi/HGO composite multilayer film, wherein the more the times of alternate immersion are, the thicker the thickness of the Chi/HGO composite multilayer film is.

What is claimed is:

1. A method for preparing a chitosan/heparinized graphene oxide composite multilayer film on the surface of a medical magnesium alloy, which is characterized by comprising the following steps:

1) firstly preparing negatively charged heparinized graphene oxide (HGO);

2) then performing surface chemical treatment and self-assembly surface modification on the medical magnesium alloy;

3) further covalently immobilizing chitosan (Chi) on the surface of the magnesium alloy, thereby constructing a positively charged material surface;

4) alternately immersing the surface-modified magnesium alloy material in HGO and a Chi solution, and then fully adsorbing;

5) finally, obtaining the chitosan/heparinized graphene oxide composite multilayer film after drying.

2. The method for preparing the chitosan/heparinized graphene oxide composite multilayer film on the surface of the medical magnesium alloy of claim 1, which is characterized in step 1), a method for preparing the heparinized graphene oxide comprises the following steps:

1.1) firstly, ultrasonically dispersing graphene oxide in an NaOH solution having a concentration in the range of 0.1 to 0.5 mol/L for 2 hours;

1.2) then adding excess chloroacetic acid to ultrasonically react for 2 to 4 hours;

1.3) repeatedly and centrifugally washing the solution to be neutral to remove impurities to obtain carboxylated graphene oxide;

1.4) ultrasonically dispersing the resulting carboxylated graphene oxide;

1.5) adding to a mixed solution of N,N'-dicyclohexylcarbodiimide and 4-(dimethylamino)pyridine to perform an oscillation reaction for 2 to 4 hours;

1.6) repeatedly and centrifugally washing the solution to remove impurities;

1.7) adding the activated graphene oxide to a heparin solution to fully react for 4 to 12 hours; and 1.8) finally obtaining heparinized graphene oxide after repeatedly centrifugal washing.

3. The method for preparing the chitosan/heparinized graphene oxide composite multilayer film on the surface of the medical magnesium alloy of claim 2, which is characterized in step 1.5), the molar ratio of N, N'-dicyclohexylcarbodiimide and 4-(dimethylamino) pyridine is 3 to 1 in the mixed solution of N, N'-dicyclohexylcarbodiimide and 4-(dimethylamino) pyridine.

4. The method for preparing the chitosan/heparinized graphene oxide composite multilayer film on the surface of the medical magnesium alloy of claim 1, which is characterized in step 2), the chemical treatment on the magnesium alloy surface comprises the following steps:

firstly washing the magnesium alloy and then immersing in the NaOH solution having a concentration in the range of 1 to 5 mol/L and treating at a temperature of 60 to 85° C. for 8 to 24 hours.

5. The method for preparing the chitosan/heparinized graphene oxide composite multilayer film on the surface of the medical magnesium alloy of claim 1, which is characterized in step 2), the self-assembly method comprises the following steps:

immersing the magnesium alloy treated by NaOH into a 16-phosphonohexadecanoic acid solution having a concentration in the range of 1 to 10 mmol/L for 12 to 24 hours, and taking a sample out and then treating in vacuum at a temperature of 110° C. for 12 to 24 hours.

6. The method for preparing the chitosan/heparinized graphene oxide composite multilayer film on the surface of the medical magnesium alloy of claim 1, which is characterized in step 3), the covalent immobilizing method of chitosan comprises the following steps:

3.1) immersing the surface-modified sample obtained in step 2) in a mixed solution of N-(3-dimethylaminopropyl)-N'-ethylcarbodiimide/N-hydroxysuccinimide to react;

3.2) drying after reacting for 2 to 8 hours;

3.3) after drying, continuously reacting by immersing in a chitosan solution having a concentration in the range of 1 to 5 g/L;

3.4) after continuously reacting for 2 to 8 hours, washing and drying the sample to obtain a chitosan-modified positively charged magnesium alloy.

7. The method for preparing the chitosan/heparinized graphene oxide composite multilayer film on the surface of the medical magnesium alloy of claim 6, which is characterized in step 3.1), the molar ratio of N-(3-dimethylaminopropyl)-N'-ethylcarbodiimide to N-hydroxysuccinimide is 4 to 1 in the mixed solution of N-(3-dimethylaminopropyl)-N'-ethylcarbodiimide/N-hydroxysuccinimide.

8. The method for preparing the chitosan/heparinized graphene oxide composite multilayer film on the surface of the medical magnesium alloy of claim 1, which is characterized in step 4), the method for preparing the chitosan/heparinized graphene oxide composite multilayer film comprises the following steps:

alternately immersing the material obtained in step 3) in the heparinized graphene oxide having a concentration in the range of 0.1 to 1 mg/ml and the chitosan solution having a concentration in the range of 1 to 5 g/L, adsorbing for 20 to 60 minutes every time, and then fully drying after adsorbing every time, thereby obtaining the chitosan/heparinized graphene oxide composite multilayer film.

9. The method for preparing the chitosan/heparinized graphene oxide composite multilayer film on the surface of the medical magnesium alloy of claim 8, which is characterized in that the more the times of alternate immersion are, the thicker the thickness of the chitosan/heparinized graphene oxide composite multilayer film is.

* * * * *